(12) United States Patent
Miñano Fernandez

(10) Patent No.: US 9,173,476 B2
(45) Date of Patent: Nov. 3, 2015

(54) CHEWING-BASED ORAL SELF-CLEANING DEVICE

(76) Inventor: Fernando Miñano Fernandez, Madrid (ES)

( * ) Notice: Subject to any disclaimer, the term of this patent is extended or adjusted under 35 U.S.C. 154(b) by 85 days.

(21) Appl. No.: 14/126,549

(22) PCT Filed: Jun. 15, 2012

(86) PCT No.: PCT/ES2012/070445
§ 371 (c)(1),
(2), (4) Date: Dec. 16, 2013

(87) PCT Pub. No.: WO2012/172149
PCT Pub. Date: Dec. 20, 2012

(65) Prior Publication Data
US 2014/0123421 A1    May 8, 2014

(30) Foreign Application Priority Data

Jun. 17, 2011 (ES) .................. 201100696

(51) Int. Cl.
| *A46B 9/04*  | (2006.01) |
| *A61C 17/00* | (2006.01) |
| *A61H 13/00* | (2006.01) |
| *A46B 15/00* | (2006.01) |
| *A46B 9/06*  | (2006.01) |
| *A46B 1/00*  | (2006.01) |
| *A46B 5/00*  | (2006.01) |

(52) U.S. Cl.
CPC . *A46B 9/045* (2013.01); *A46B 9/06* (2013.01); *A46B 15/0016* (2013.01); *A46B 15/0075* (2013.01); *A46B 15/0081* (2013.01); *A46B 1/00* (2013.01); *A46B 5/00* (2013.01); *A46B 2200/1026* (2013.01); *A46B 2200/1066* (2013.01); *A46B 2200/1086* (2013.01); *A61C 17/00* (2013.01); *A61H 13/00* (2013.01)

(58) Field of Classification Search
CPC ............... A46B 9/045; A46B 15/0075; A46B 2200/1026; A46B 2200/1066; A46B 2200/1086; A61H 13/00; A61C 17/00
USPC ........... 15/167.2; 601/139–141; 606/234, 235
See application file for complete search history.

(56) References Cited

U.S. PATENT DOCUMENTS

| 3,335,718 | A | * | 8/1967 | Sexton .......................... 601/139 |
| 4,059,101 | A | * | 11/1977 | Richmond .................... 601/139 |
| 4,428,091 | A | | 1/1984 | Janssen |
| 5,175,901 | A | | 1/1993 | Rabinowitz |
| 5,615,443 | A | | 4/1997 | Lai |
| 2002/0083539 | A1 | | 7/2002 | Bella |
| 2006/0085933 | A1 | * | 4/2006 | Meyman ...................... 15/167.2 |
| 2011/0072605 | A1 | | 3/2011 | Steur |

FOREIGN PATENT DOCUMENTS

| CL | 200202671 | 9/2003 |
| CO | 5750038 A1 | 4/2007 |

(Continued)

*Primary Examiner* — Mark Spisich
(74) *Attorney, Agent, or Firm* — Richard M. Goldberg

(57) ABSTRACT

A chewing-based oral self-cleaning device includes a pair of tubes (2, 3) placed back to back either directly or separated by a base plate (13), optionally provided with an external handle (1) and a positioning flange (15). Each of the tubes includes a channel (14) into which the teeth are inserted and each channel is provided with side drag elements and descaling elements on the base thereof.

13 Claims, 12 Drawing Sheets

(56) References Cited

FOREIGN PATENT DOCUMENTS

| | | |
|---|---|---|
| EP | 0312462 A1 | 4/1989 |
| EP | 0419587 B1 | 8/1990 |
| EP | 0449152 A1 | 3/1991 |
| EP | 0951225 B1 | 5/1998 |
| ES | 474540 A1 | 2/1979 |
| ES | 2035121 T3 | 9/1988 |
| ES | 2095933 T3 | 3/1997 |
| GB | 2457665 * | 8/2009 |
| IE | 84097 | 12/2005 |
| JP | 2-206403 * | 8/1990 |
| JP | 7-8321 * | 1/1995 |
| MX | PA05010179 A | 5/2006 |
| MX | 2009011596 A | 11/2009 |
| WO | 90/14802 * | 12/1990 |

* cited by examiner

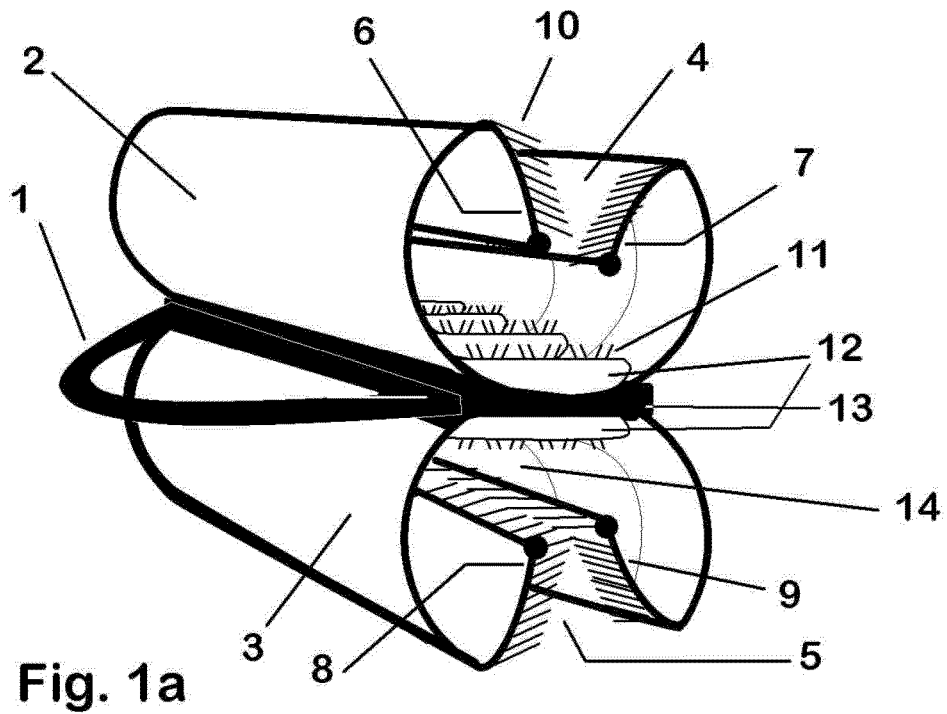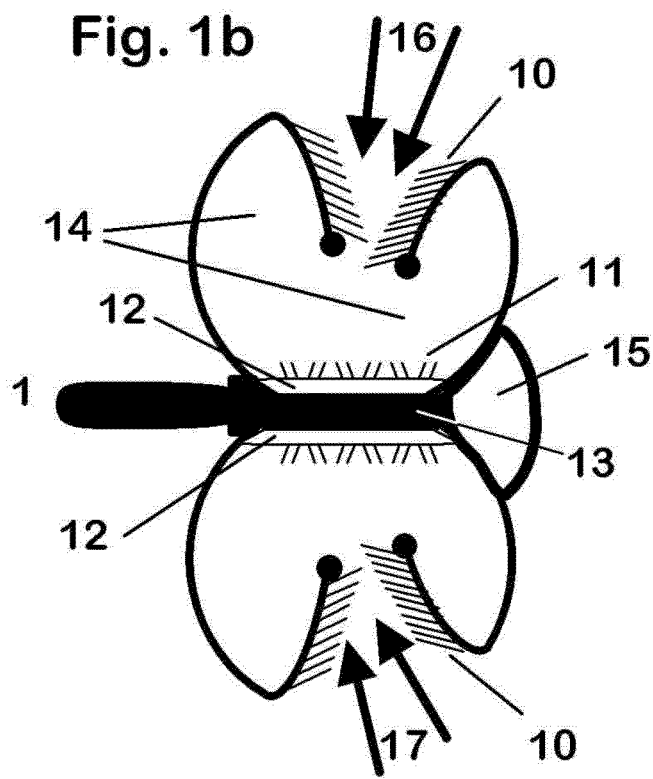

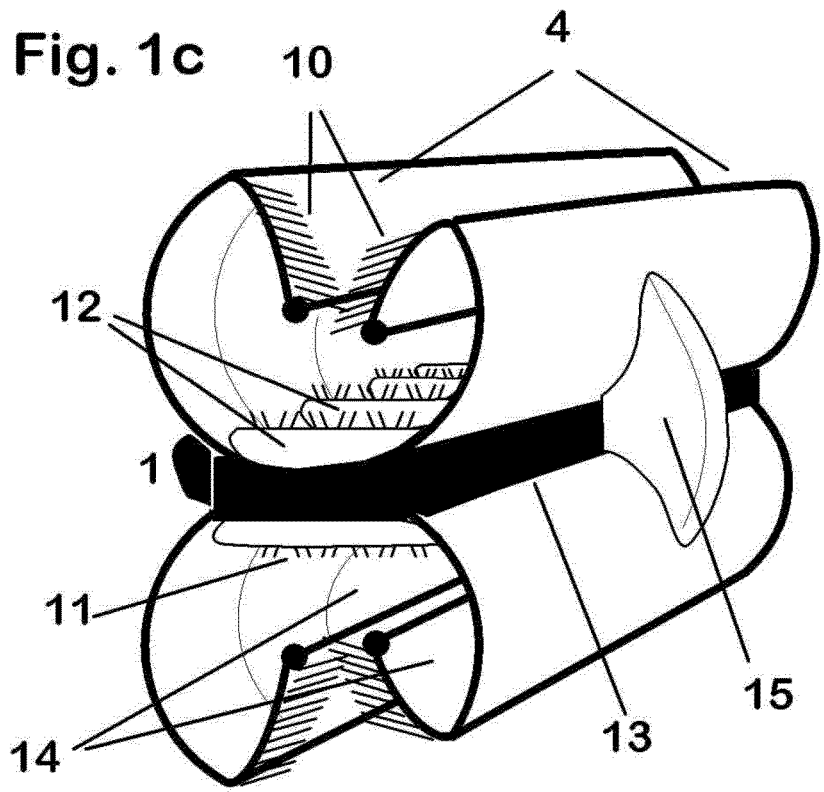
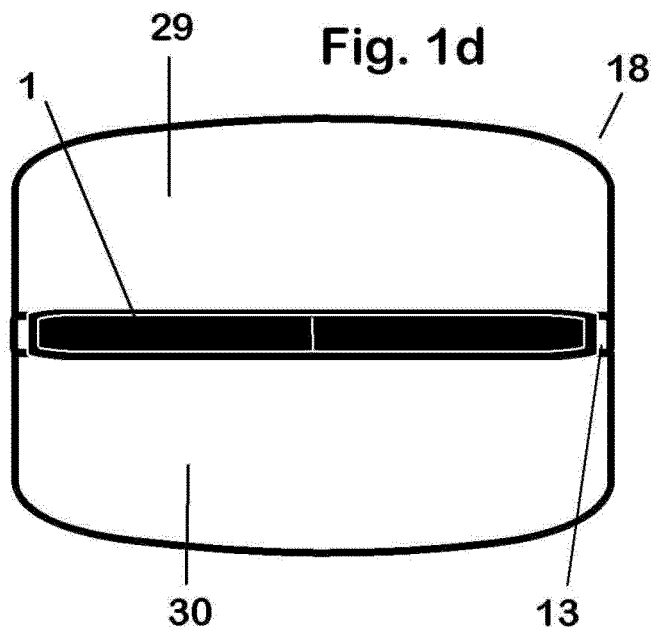

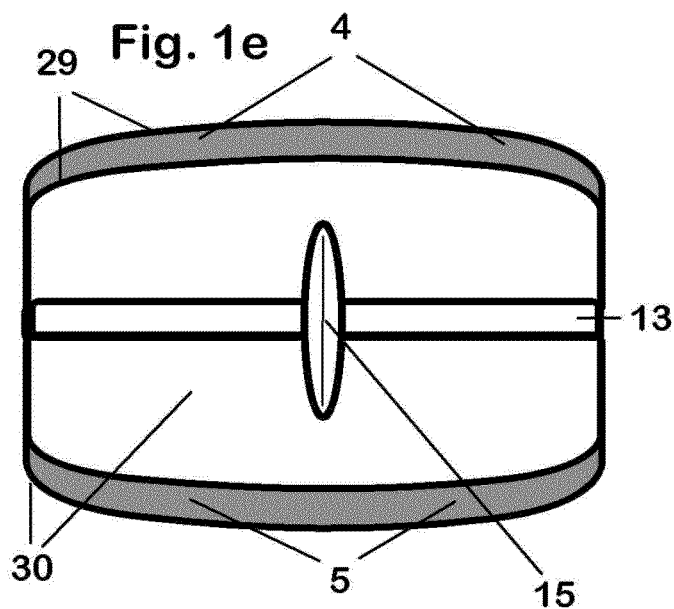
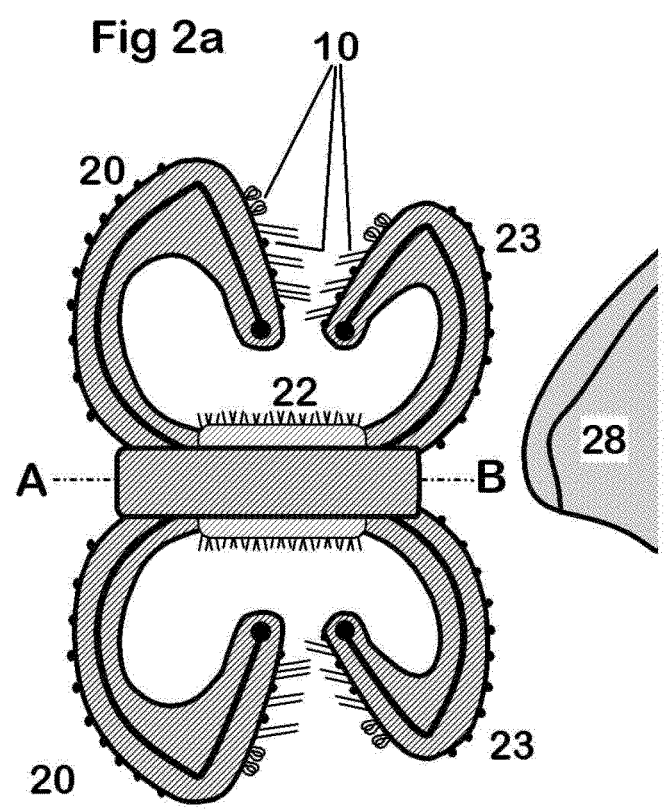

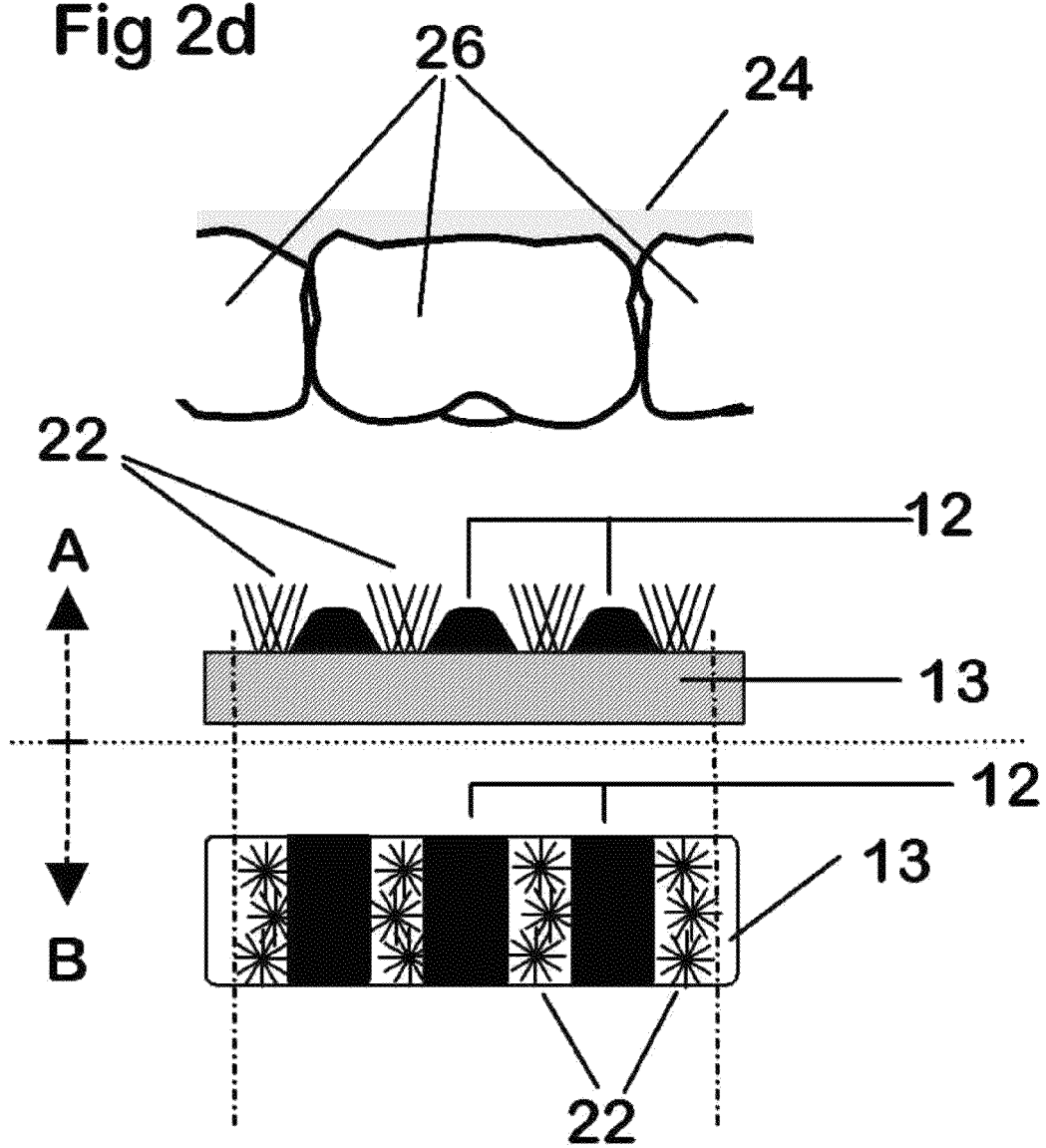

CHEWING-BASED ORAL SELF-CLEANING DEVICE

BACKGROUND OF THE INVENTION

This invention refers to an oral self-cleaning device which works only through maxillary movement, similar to the action performed when chewing gum, which comprises interior cleaning ailerons provided with drag and raking items made up of a set of bristles, protrusions and scraping rasps or "radulas".

1. Technical Sector

The technical sector involved in this invention is that of dental cleaning and oral hygiene devices.

2. State of the Art

Everyday oral hygiene is currently performed with toothbrushes comprising a handle, with more or less sophisticated shapes and bristle design, with or without devices for dispensing products for washing. These can be electrical, working by means of rotation, vibration, ultrasounds, amongst others. Also used for cleaning the interproximal spaces of teeth is dental floss, which can be set on a frame, or withdrawn from a continuous dental floss dispenser.

All these utensils must be used with one or both hands. Although they are handled from outside, the action performed by them takes place inside the mouth. The effectiveness of the cleaning will depend on the user's skill and the characteristics of the utensil.

There are numerous inventions connected with devices for dental hygiene.

Different applications refer to electric or manual brushes either provided with toothpaste or not, with a fixed or removable head. One example of this is given in ES2035121T3 or MX2009011596. One can also find different inventions involving a support for dental floss, such as EP0449152, CO5750038A1, MXPA05010179 or CL26712003, amongst others, for example.

There are also inventions as regards the material of which the cleaning bristles are made, such as for example EP0951225.

Disposable dental cleaning devices have also been described. One example that can be found is EPO419587.

We now detail the technical limitations of oral hygiene according to the state of the art.

1. Unavoidable use of the hands during the cleaning operation;
2. Difficulty entailed by reaching certain zones that are hard to access or concealed, as occurs with the lingual side of the teeth, the inter-proximal spaces between the teeth, or at the bottom of the cheeks near the mandibular articulation.
3. An added limitation is involved for the disabled, the sick and bedridden and other cases who, for some cause involving the psychomotor faculties, cannot use their hands or find it very difficult to use them to carry out their own oral hygiene, or in the case of children.
4. Size and weight of some cleaning devices. One example of these are the electrically operating ones which entail some difficulty for transporting or even for travelling with them, along with their charger.
5. The order and methodical discipline which have to be imposed to carry out good oral cleaning, as one has to successively treat the different facets of the dental crown. One after another, the teeth have to be cleaned in five phases: for example, first on their vestibular side (exterior), secondly on the lingual side (interior), thirdly on the occlusal side (the side facing the antagonistic teeth) and fourthly in the inter-proximal spaces between the teeth. This has to be done for the upper teeth arch and afterwards for the lower ones. Lastly the oral mucosa has to be dealt with, especially the gums.
6. Time needed for brushing teeth and use of dental floss. Of course all the time required has to be devoted to this if one wishes to comply with what is stated in the previous paragraph.
7. The muscular effort and lack of comfort involved in keeping the hands and mouth in strained positions. In the execution of manual brushing or even electric brushing and the use of dental floss, the mouth has to be kept open, with the disadvantage for the weak or very tired, placing of the brush in order to reach difficult places, apart from the discomfort that all of this may involve.
8. Energy use in modern electrical models. A power source is needed, either through the consumption of batteries or supplying these from the electrical mains.
9. There is a need to handle massage of soft zones, such as the periodontal areas close to the teeth, such as gums, lips, cheeks and tongue, where one has to expressly use the special rough surfaces designed for this purpose, generally on the back of the conventional type brush, for example;
10. The noise made in brushing the teeth, above all with electrical type devices.
11. The consequences of excessive force and/or repetition on applying the manual brush for example, in oral hygiene. This can in fact go as far as to cause acute and chronic traumatisms, such as acute lesions and cracks in the gums (Stillman cracks), the withdrawal of the gums, generating open dental necks, loss of wedge substance at the root zone close to the dental crown, amongst other disorders. There are often doubts about how hard and the number of times one has to brush in order to ensure dental hygiene.
12. The need to use a cleaning agent such as a toothpaste;
13. The need to buy several items and apparatus (normal brush, inter-proximal brushes, dental floss etc.) to ensure proper oral hygiene, at the economic and ecological cost that this involves.
14. The artificial, strained and uncomfortable nature of conventional or current oral hygiene, by inserting all the items mentioned in the mouth, one after another.
15. Cleaning with plenty of water to remove the toothpaste, and even so fibres of meat or vegetables are left between the bristles of a conventional brush.
16. The handling problem represented by cleaning the teeth of an animal by professionals involved in animal handling such as vets, stockbreeders, carers, breakers/tamers, trainers, owners etc., when they wish to carry out hygienic brushing of the teeth with some regularity on pets such as dogs and cats, domestic animals, zoo or wild animals, with any degree of safety.

This party has not found any antecedent with the characteristics of the invention proposed. The advantages will be put forward below.

SUMMARY OF THE INVENTION

The invention now being put forward consists of a chewing-based self-cleaning oral device, which is made up of a semi-rigid extended body comprising two tubes tangentially and longitudinally back to back. Each of these tubes is open lengthways in zones opposite to the base plate, open along the tangential lines opposite to the joining zones, in which each of the openings comprises a section or ailerons facing the inside of the tube in which these are located, forming longitudinal slits that create an upper and lower cleaning channel. The tubes can have different sections, in cylindrical or prismatic shape, for example. In the zone where the tubes back onto each other there is a base plate provided on the outside with a fitting handle and on the inside with a positioning flange in a location opposite to the fitting handle.

On the inside of the tubes, beside the base plate or zone where the tubes back onto each other, there are undulating strips at the front towards the openings and a set of brushes, protrusions and scraping rasps or "radulas" in the outer portion of the sections facing the interior.

The body thus has a transversal section basically in the shape of a capital H, with curved arms, made up of the base plate and the two tubes to which this is joined on each side.

The teeth in both tooth arches fit into the cleaning channels while chewing. The sections or flanges facing the inside of each tube and which form the respective channels, as has been stated, project towards the interior in the channel, so as to form cleaning ailerons fitted with a set of cleaning, massage and dragging items as mentioned above, which are firmly fitted and positioned so as to oppose the entry and exit route of the teeth while chewing.

The operation involves the following stages:
1. Inserting the self-cleaning device into the mouth by means of the handle, positioning this in the area to be treated with the aid of the tongue, and holding this with the teeth.
2. Biting the self-cleaning device at the cleaning channels, thus meaning that the upper and lower teeth will fit into and penetrate the respective tubes of the device, which will be forced open by the penetration of the teeth at the same time as constantly pressing the dental surface which is penetrating them; the tubes are supple and resistant; in this stage the tooth will slide over the first cleaning item, which is of the dragging type, which will not represent any obstacle for the penetration of the tooth due to the angle at which this is placed.
3. While the self-cleaning device is being bitten, going in as far as certain buffer strips located beside the base plate set between the two tubes, where contact with a second cleaning agent takes place, that we call the descaler which, like a chisel, will eliminate any organic matter sticking to the occlusal side of the teeth, particularly on the premolar and molar teeth with greatest occlusal surface area.
4. By slightly separating the jaws, the pressure that was being applied by the teeth on the buffer strips is slackened, so that the teeth, in their travel, but without coming right out of the device, come up against certain ailerons or portions of the tubes facing the interior of said tubes, whose angle opposes the exit of the tooth and consequently that of anything sticking to their surface, by means of their scraping and raking items; the morphology of the bristles with bevelled tips and also the presence of protrusions and scraping rasps means that any adhering organic material is dragged along, removing this and leaving the tooth clean; the chewing motion must be repeated several times in each dental zone to ensure satisfactory cleaning, which will be achieved by repeated chewing motions without completely releasing the device with the teeth.
5. The material pulled off, along with the saliva present everywhere, will circulate through the channels of the self-cleaning device to its exterior in the oral cavity.
6. After cleaning the first dental zone the apparatus is redirected by sliding towards an adjacent area of teeth, which can be done simply by separating the jaws slightly and loosening the device trapped between them a little. The device is thus released so then, with the aid of the tongue, lateral pressure can be exerted on the positioning flange to be able to slide the device and make this move easily over the dental arch, repositioning this in the following zone not yet treated to be able to go on cleaning with a simple chewing operation.

Depending on the dimensions of a basic embodiment of the invention, four positions would be enough to complete the entire dental cleaning operation, for example a first position for right-hand molars and premolars, a second position for the right-hand canine teeth and incisors, a third position for the left-hand canine teeth and incisors and a fourth position for left-hand premolars and molars.
7. The device can at any time be cleaned in different ways, from a simple rinse under the tap with the fingers, to an intensive cleaning with brushing, use of chemical or biological agents and/or a thermal disinfection.

As has been pointed out above, this device has a longitudinal slit along each tube, through which the teeth penetrate when biting, forcing and extending the opening angle as the tooth gradually penetrates in the bite, as a gradually greater tooth volume (incisors, canine teeth, premolar and/or molar) goes in between the sides of the gap.

The opening angle of the cleaning ailerons can be adjustable while at rest (FIGS. 5d and 5e) as this can be fitted with a mechanism for adjusting the elastic tension of the tubes, for example by means of a screw-type regulator operated by means of the handle, which rotates and pushes the walls of the tube like a ram; or in another option, this comprises a regulator in the base plate, tightening which will make the walls, edges and cleaning ailerons of the tubes converge with each other more or less.

When the upper teeth go into the slit in the upper tube, the lower teeth also go into the lower tube, forcing to one side the structure which acts like stays or a warp against the motion of the teeth, constituted by dragging items comprising a scraping rasp, bristles and protrusions, and which are arranged on both sides of the slots extending as far as into the inside of each cylinder. They are nevertheless always placed in favour of the arch penetration, so that they allow the tooth in easily, but grip it firmly on its vertical surface when it comes out, thanks to the great tubular elasticity. This means that the drag items act like a chisel against any remains of food and bacterial plaque adhering to the surface of the teeth, eliminating these by their effect of "brushing up the wrong way", for them to be drained along with the saliva out of the channels towards the mouth of the oral cavity.

At the bottom of each tube cavity, where the tubes join, the teeth will be halted, as is particularly the case of molars and premolars, which will come up against a set of items at this bottom, comprising protrusions and bristles in several directions which will also be obliquely opposed to the occlusal face of the teeth. These are the occlusal bristles, which act as descaling items arranged between the undulating buffer strips of the base plate which lies between the teeth, in such a way that each time a molar, for example, comes up against this set of items, these items exert leverage on any remains of food like a chisel until these are pulled off. So that these are not squashed by the molars, the bristles are partly protected by certain ridges or hard buffers of lower height, which limit the advance of the tooth while chewing.

The cleaning can start at any point of the tooth arch, for example from the right-hand molar zone, and from there, after several chews in this dental zone, the jaws are slackened to then gradually slide the device with the aid of the tongue by pushing on the external pushing flange of the device in the middle of its lingual side, moving this to the left along the arches, towards the sides of the mouth. It will thus successively complete the entire dental cleaning, covering the rest of the dental areas (right-hand premolars, incisors, left-hand premolars and left-hand molars). This can nevertheless be repeated as many times as are necessary on both sides.

The cleaning operation will ensure that both food remains and also any dental plaque are removed from the surface of the teeth; the soft parts of the mouth are also massaged by the scraping and massage items in the form of protuberances on the surfaces of the device, which will act on the neck of the teeth, the gums and other soft mouth zones such as the tongue, lips and cheeks.

ADVANTAGES OF THE DEVICE PORTRAYED IN THE INVENTION

As opposed to the disadvantages stated above, this invention provides the following advantages:

1. The device portrayed in this invention is specially designed to be used with no hands, except for the initial insertion into the mouth and its final extraction. This means that, while users are cleaning their teeth with the device, they can perform other tasks at the same time, from driving, working with the computer to carrying out household tasks. It is as if they were chewing gum.
2. The device reaches practically all the areas that are important as regards cleaning, since its design includes different strategically positioned and distributed items for dragging, such as bristles, protrusions or scraping rasps, which reach practically everywhere that food could have spread.
3. One does not have to brush with one's hand, as it is enough to insert the apparatus, chew repeatedly and remove this at the end to wash this under the tap. The cleaning will be done passively, by chewing, but effectively and above all efficiently.
4. The size of the self-cleaning device will be approximately half that of a folded set of reading glasses and its weight is like a pocket lighter's, meaning it can be conveniently carried in the pocket.
5. All of this is done in a single operation, as the self-cleaning device will gradually move between the tooth arches thanks to being pushed by the tongue, handling the consecutive zones of the two (upper and lower) arches as it goes along these, on all sides of the teeth, including the gums and other oral mucosa, as was stated, just with the to-and-fro motion of the jaws, as if the user were chewing gum.
6. The self-cleaning device can take at most one tenth of the time required to clean the teeth with today's conventional systems.
7. With this device the cleaning operations are done from inside, naturally and conveniently, as only the jaws (maxilla and mandible itself) are used, without separating the lips.
8. This is totally ecological, without any use of external energy, as only the jaws and the tongue work.
9. The strategic distribution of the areas with bristles, protrusions and scraping rasps over the surface of the object of the invention will massage the soft zones without our noticing this, gently and naturally, as this is similar to the contact with food when this is being chewed.
10. This is practically inaudible, as the noise is less than we make when we chew gum with our mouths closed, since the chewing angle is small and the arches do not even make any impact, as this is prevented by the self-cleaning device which gets in the way. This dampens the contact of the jaws thanks to the buffer strips located in the base plate. It is just at this time when the occlusal faces are cleaned, at the point where the teeth would otherwise hit each other.
11. Our jaw is much more delicate when chewing and no injuries are produced with the self-cleaning device, and one cannot even bite one's tongue when using this. With this device the force of the jaws does not matter much, as the dragging items of the self-cleaner never point the opposite way to our oral mucosa nor that of the teeth (gingival line). They only provide mechanical opposition against the remains of food and the dental microbial plaque adhering to the teeth, as it is when the tooth moves away, when the jaw is opened, that the dragging items inside the cleaning ailerons will pull these off. Thanks to the elastic pressure of the cylinder they will thus have a dragging and raking effect on the sediments adhering to the tooth.
12. The self-cleaner can be used with or without toothpaste. It is enough to rinse out the mouth when finishing, or if desired, to add a little mouthwash in the dental hygiene operation. In the event of using toothpaste a great deal less will be consumed, a quarter of the amount formerly needed, as the dragging items are shorter and more spread out, a liquid toothpaste being the most recommendable.
13. With the compact self-cleaning device in a single piece, although the cleaning is not so specific and intense, this is nevertheless performed more often and this handles the whole operation conveniently and thus in this case it will be one for all. Economically and ecologically the advantage is obvious.
14. This is a natural biting system, as if we were chewing food, more gently even, since the opening of the jaw is small and convenient, even not as hard as when one is eating certain foodstuffs. Quickly, in roughly fifteen chews or movements of the jaws, the bacterial plaque will gradually be destroyed and the remains of food sticking to the surfaces of the teeth will be eliminated.
15. Simply moving the finger between the dragging and descaling items, which are short and thin, rinsing these under the tap or in a little liquid with mild mouthwash could be enough.
16. With the self-cleaning device the operation will be easier as it is the animals themselves which will clean their own teeth, practically without being forcing to do so, as it is only required to trick them by impregnating the interior of the apparatus with some substance that they like (sweet, meat flavour, etc.).

BRIEF DESCRIPTION OF THE DRAWINGS

In order to illustrate the following explanation, twelve sheets of drawings are adjoined to this descriptive report, in which twenty-two figures represent the essence of this invention as an example, and in which:

FIG. 1a Perspective of the outer lateral side or labial side of the self-cleaning device;

FIG. 1b Side view of one end of the self-cleaning device after being fitted in the user's mouth:

FIG. 1c Perspective of an inner side or lingual side view of the self-cleaning device;

FIG. 1d Outer or labial view of the fitted self-cleaning device, from outside the mouth;

FIG. 1e Interior or lingual view of the fitted self-cleaning device from the tongue;

FIG. 2a Lateral cross-section view of the self-cleaning device; in this Figure A represents a front (labial) view and B represents a lingual view of the device;

FIG. 2d Buffer strips and descaling items for the occlusal dental zones; in this Figure A represents a front view of the device and details of the projection of the teeth on the buffer strips; and B represents an occlusal view of the apparatus (the side where the tooth would meet its antagonist during chewing);

Figure 2B:
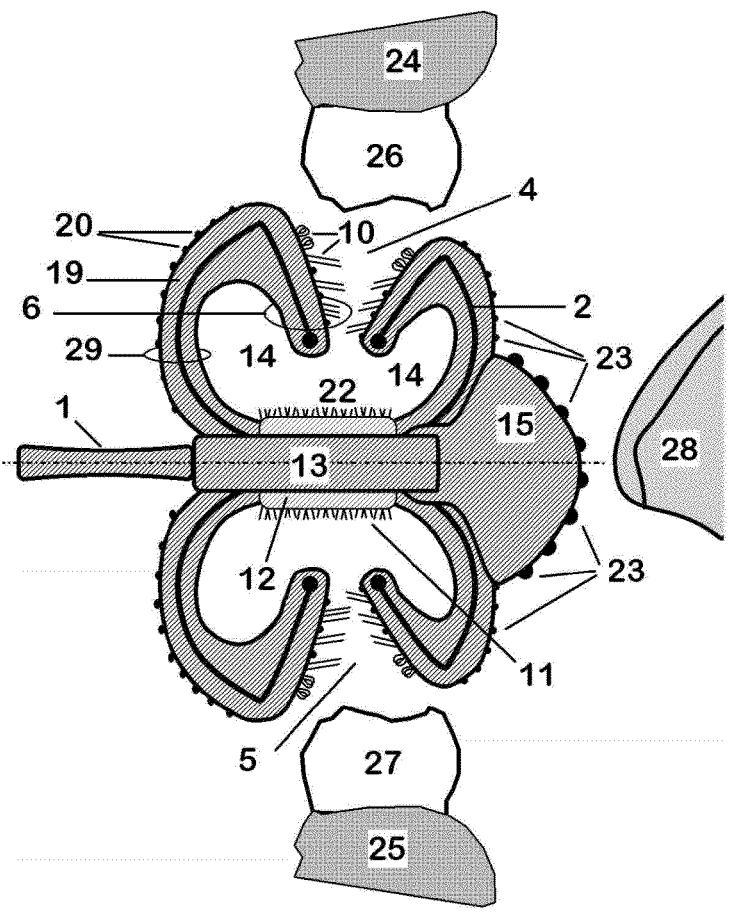
FIG. 2b Left-hand lateral central cross-section of the device showing the fitting handle and positioning flange.
Figure 2C:
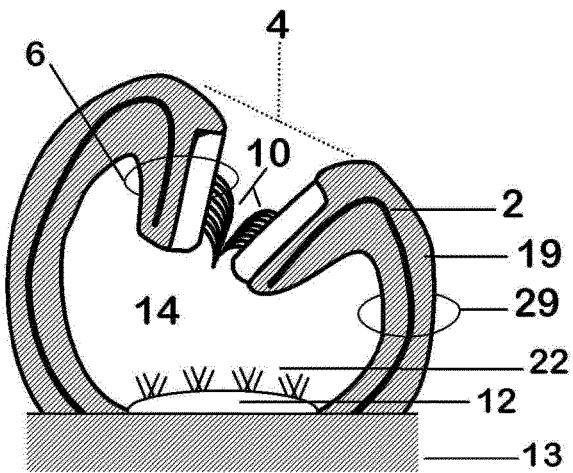
FIG. 2c Structures and cleaning items for dragging and descaling in a section of the upper tube.
Figure 3A:
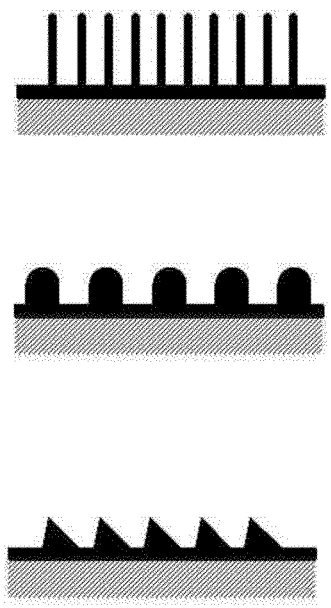
FIG. 3a Single cleaning items (bristles, protrusions and scraping rasp)
Figure 3B:
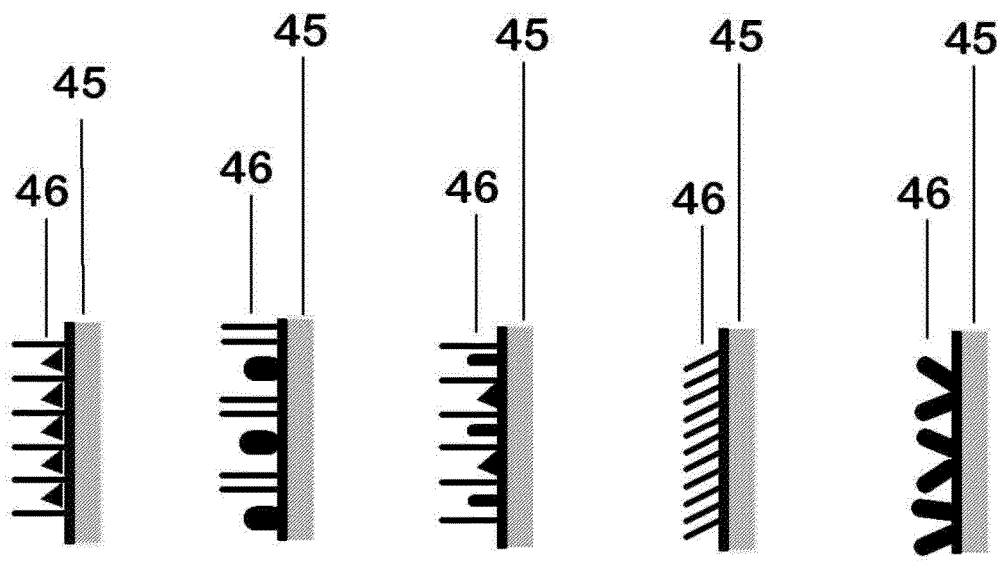
FIG. 3b Different combinations and arrangements of cleaning items (bristles, protrusions and scraping rasp)
Figure 4:
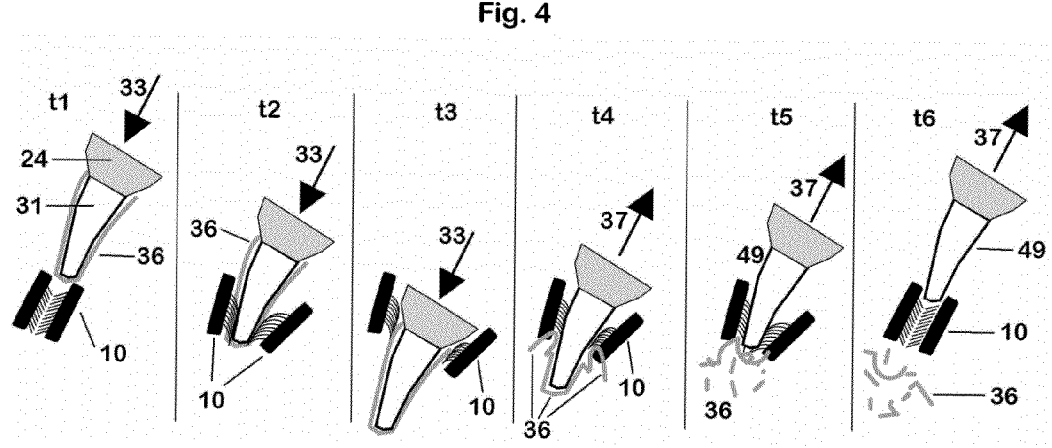
FIG. 4 Stages in the dragging cleaning in which t1 to t6 show an ordered sequence of points in the cleaning of the dirty tooth by the cleaning items until this produces a clean tooth.

The following numerical references are used in these figures:

1 Fitting handle
2 Upper tube (frame of the upper tube without casing)
3 Lower tube (frame of the lower tube without casing)
4 Upper cleaning channel
5 Lower cleaning channel
6 Upper labial cleaning aileron
7 Upper lingual cleaning aileron
8 Lower labial cleaning aileron
9 Lower lingual cleaning aileron
10 Dragging items (bristles, protrusions and scraping rasps)
11 Descaling items (occlusal bristles)
12 Buffer strips
13 Base plate
14 Cleaning channel
15 Positioning flange
16 Upper teeth biting in through the slit
17 Lower teeth biting in through the slit
18 Detail of the rounded end
19 Elastomeric mould
20 Protrusions and scraping rasp for oral cleaning
21 Dragging bristles
22 Occlusal descaling bristles
23 Protrusions and scraping rasp for lingual cleaning
24 Upper gum
25 Lower gum
26 Upper molar
27 Lower molar
28 User's tongue
29 Upper tube (upper cylinder+casing)
30 Lower tube (lower cylinder+casing)
31 Upper incisor
32 Lower incisor
33 Jaw closing force (gripping force)
34 Elastic retraction of the cylinder
35 Elastic retraction of the cleaning aileron
36 Microbial dental plaque and remains of food
37 Mandibular opening force (grip-releasing force)
38 Different models of section of the cylinder or prismatic casing
39 Different models of section of the cylinder or prismatic casing
40 Different models of section of the cylinder or prismatic casing
41 Different models of section of the cylinder or prismatic casing
42 Different models of section of the cylinder or prismatic casing
43 Different models of section of the cylinder or prismatic casing
44 Succession of parallel, flexible elastic rings as an alternative to the cylinder with continuous wall
45 Wall of the tube or of the cleaning aileron
46 Different combinations and arrangements of cleaning items: bristles, protrusions and scraping rasps
47 Rotation of the fitting handle for adjusting the tension of the cylinders and regulating the convergence of the cleaning ailerons
48 Adjustment screw inside the base plate
49 Clean incisor
50 Moving the device with the tongue
51 Cylindrical frame formed by a number of half-rings in parallel
52 Frame in prismatic box formed by a set of polygonal segments in parallel
53 Hand guard of the self-cleaner for animal teeth
54 Grip fixed to the hand guard which houses the threaded rod rotating inside this
55 Stopping handle fixed to the threaded rod and which rotates on the grip to regulate the convergence of the cleaning ailerons
56 Threaded rod
57 Thread base fixed to the positioning flange of the self-cleaning device and the base plate
58 Ram which exerts pressure on the wall of the tube through the screw effect of the rod for convergence of cleaning ailerons
59 Idle rotation of the combined assembly made up of the grip, the hand guard and the ram
60 Animal tooth (horse in this case)

61 Part for joining the fitting handle with the base plate in an arch-model self-cleaning device 62 Normal route for inserting the teeth of one of the 2 arches (upper or lower) of the milk teeth of a child in an arch-model self-cleaning device 63 Tube of the arch-model self-cleaning device to clean a complete arch in a single operation and with no tongue movement.

DESCRIPTION OF THE PREFERENTIAL EMBODIMENTS OF THE INVENTION

As described above, the device put forward in the invention uses an innovative concept of the mechanics of a fairly complete oral hygiene, as the device is specially designed to be used with no hands, except for inserting this at the beginning and removing it from the mouth when finishing, with no external energy expenditure, as it only uses the mechanics of the user's mastication. Indeed, it is used to clean the teeth by the user's own to-and-fro jaw movements, chewing as if this were chewing-gum. All of this is due to its design, which will ensure an efficient hygiene that leads to the elimination of sediments adhering to the surface of the dental crown and the gums (24 and 25) after chewing the food, as pathogenic sediments. It will thus ensure cleaning the microbial dental plaque in the gingival line and inter-proximal space, apart from cleaning and massaging the oral mucosa, and it does all of this simply by chewing. Thanks to its surface area providing a scraping profile which will be placed against the dental surface, in a position which - although this does not oppose the entry of the tooth into the apparatus at the beginning, does indeed do so on its exit - when the jaw opens, it acts on the deposit of organic material adhering to the tooth and gum like a chisel or rake, descaling and dragging this off.

Figure 5A:
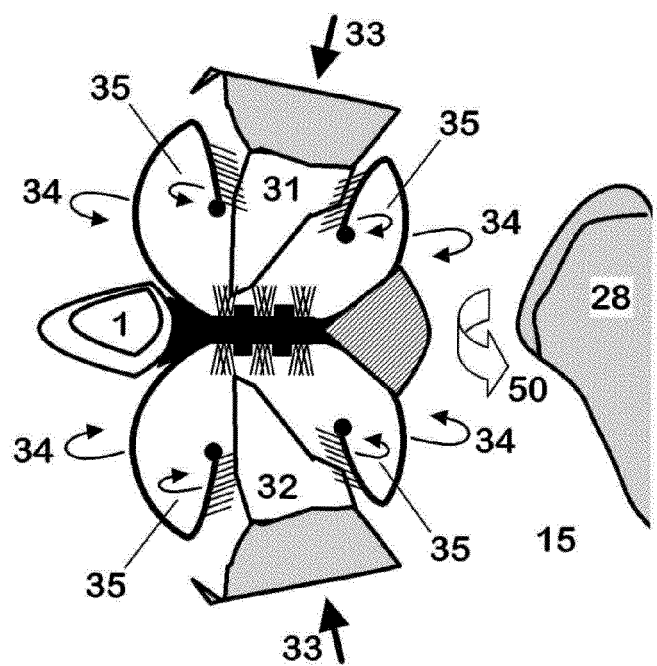
FIG. 5a Elastic retraction of the walls of the self-cleaning device through the entry of an incisor tooth and shifting this with the tongue.
Figure 5B:
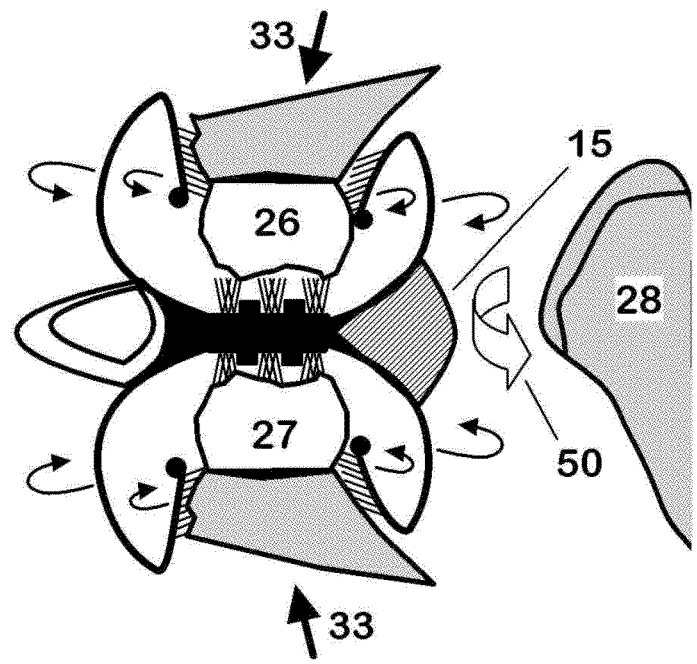
FIG. 5b Elastic retraction of the walls of the self-cleaning device through the entry of a molar tooth and shifting this with the tongue.
Figure 5C:
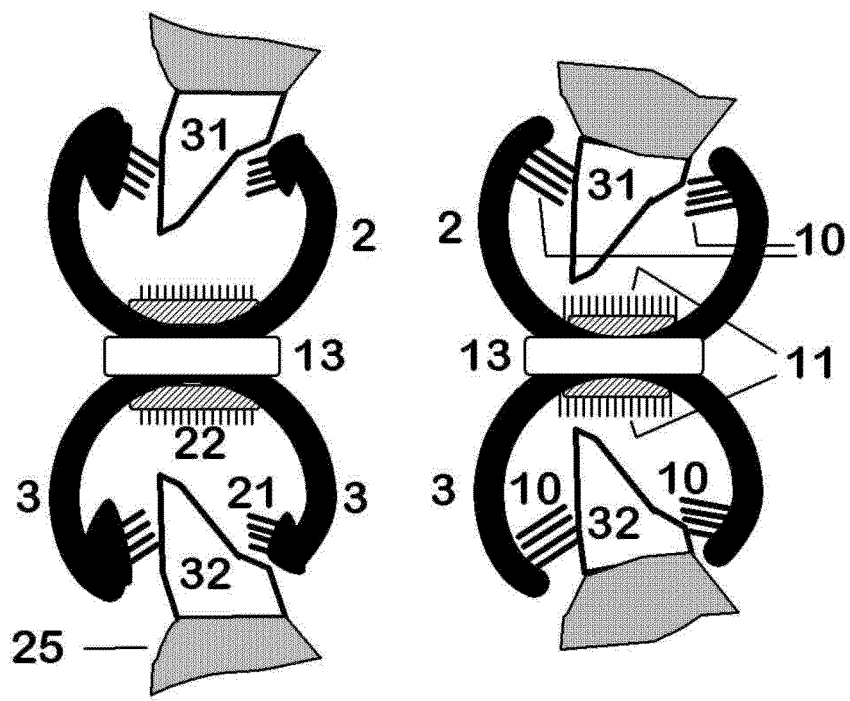
FIG. 5c Coupling of incisors in the simple model with rudimentary cleaning ailerons, and without cleaning ailerons.
Figure 5D:
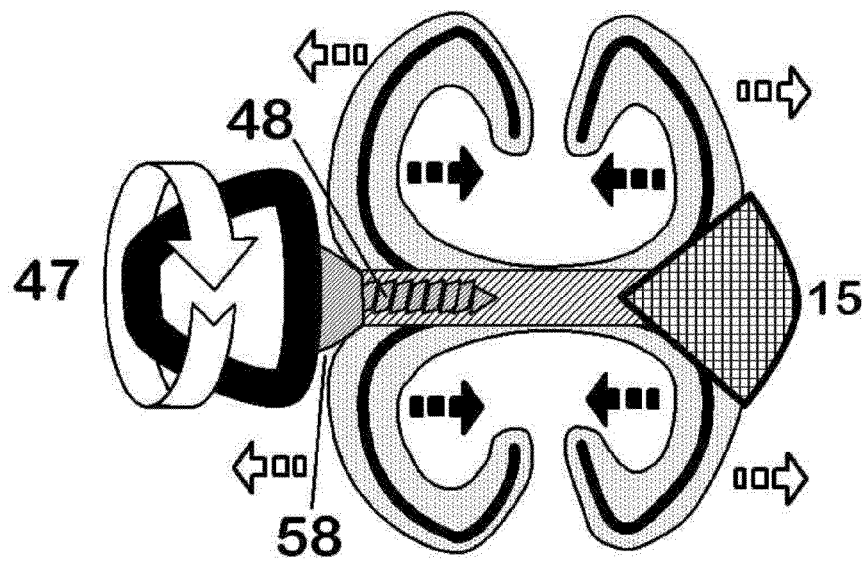
FIG. 5d Adjustment method by fitting handle with screw ram to regulate elastic tension of the convergence of the tubes and of the cleaning ailerons.
Figure 5E:
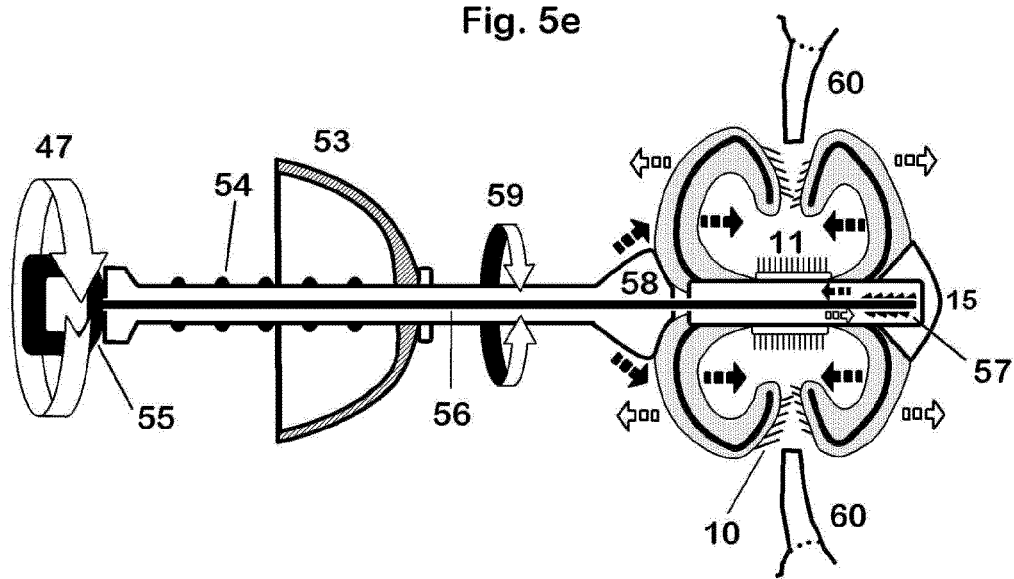
FIG. 5e Self-cleaning device for application with animals, seen in transversal section with the system of adjustment for convergence of cleaning ailerons by means of the ram pressure generated by the screw (all the parts have to be considered as sections, though they have not been drawn as such for the sake of a clear interpretation)
Figure 6A:
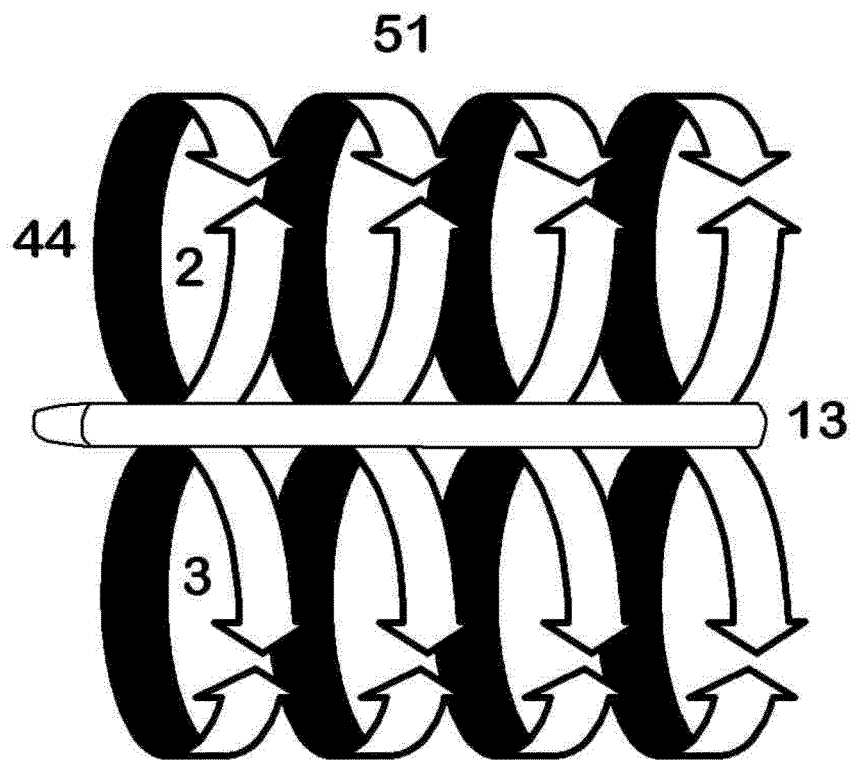
FIG. 6a Frame in an alternative cylindrical tube, made up of a number of flexible elastic half-rings set in parallel, which form a discontinuous surface.
Figure 6B:
FIG. 6b Frame in an alternative prismatic casing made up of a parallel series of elastic and flexible polygonal segments.
Figure 6C:
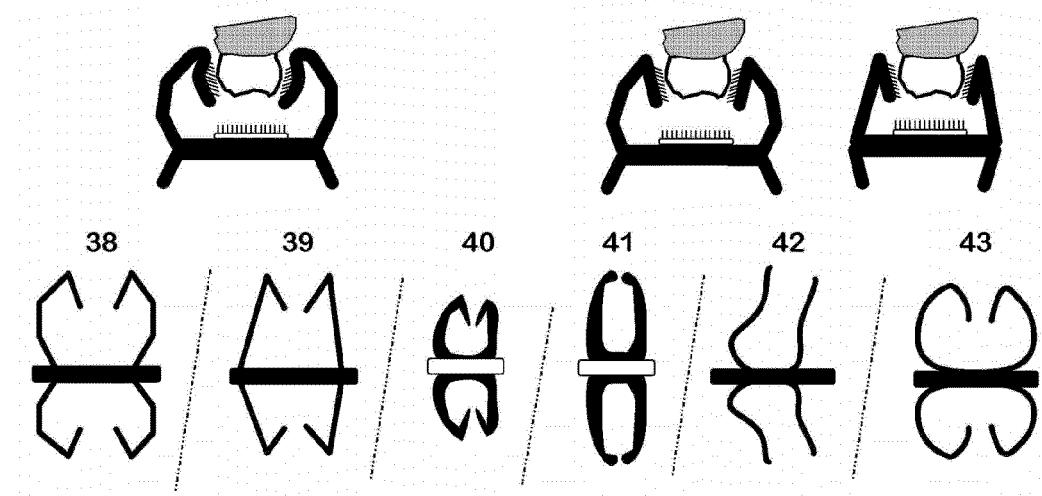
FIG. 6c Different couplings in more or less anatomical section prisms and different basic options of tubes and prismatic casings seen in cross-section.
Figure 7A:
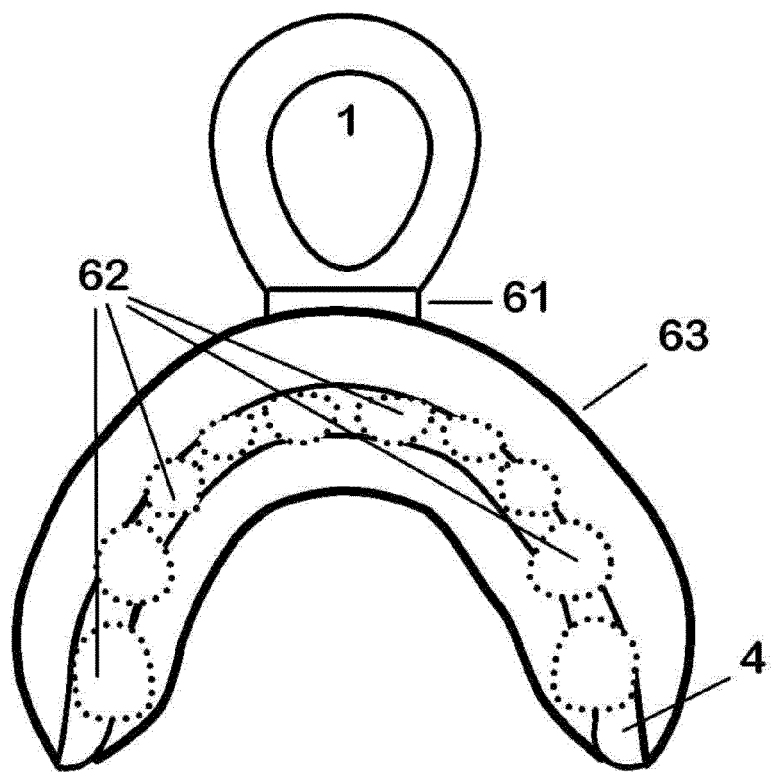
FIG. 7a Model of oral self-cleaning device in arch form for treatment of full arches for a child with the projection of the teeth in a discontinuous line and in an occlusal view.
Figure 7B:
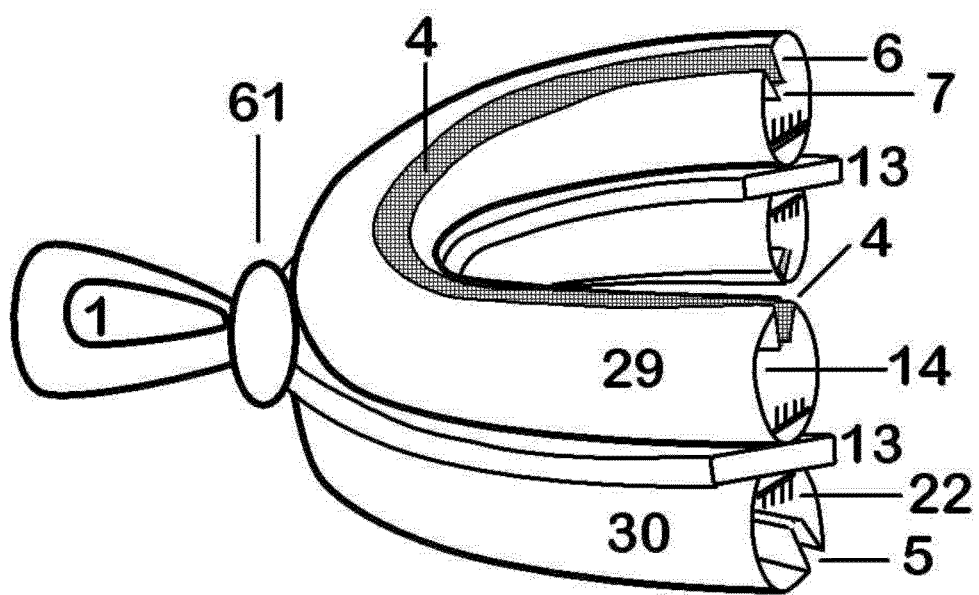
FIG. 7b Model of FIG. 7a in perspective and in upper-side view.

There is thus a description of a basic model (FIGS. 1a to 1e), examples of other models (38 to 43) as well as an arch model specially conceived for children (FIGS. 7a to 7b) or one for animal application (FIG. 5e). These are devices whose exposition is explained in the figures, sustained in the explanation given above and in the claims, where it establishes that all the forms of this invention involve the concept of a flexible and resistant elastomeric bitubular body, formed by a frame and a surrounding matrix. The skeleton or frame is comprised of two straight semi-rigid tubes (2, 3) and a highly consistent base plate (13) for joining these; the tubes respectively define an upper cleaning channel (4) and a lower cleaning channel (5) (channels 14), each provided with the semi-rigid, flexible and elastic ailerons for upper and lower labial and lingual cleaning (6, 7, 8, 9) respectively. This set, along with the cleaning channels (14), has an essentially "H"-shaped configuration. The ailerons comprise dragging items.

Each of the tubes (2, 3) comprises descaling items (11) in its lower part, in the zone where these join the base plate (13). In order to prevent these from being squashed by repeated biting, the descaling items (11) are arranged on undulating buffer strips (12). The side ends of the device are rounded off. These rounded ends, given number (18), are open at their ends, thus constituting a drain for the remains from cleaning out into the oral cavity.

Each pair of ailerons (6, 7, 8, 9) defines a cleaning channel (14) through which the tooth (or teeth) (26, 27, 31, 32, 49, 60) will go.

On the internal side of the base plate (13) between the two tubes there is a positioning flange (15) which can be moved with the tongue (28). The outer side of this base plate (13) comprises a handle (1) which will be used for its manual placing and removal, or for holding this, in the case of animals or small children.

The tubes (2, 3) could comprise an elastomeric casing on the inside and/or outside; the tubes fitted with this casing are represented by numbers (29) and (30). This casing rounds off the shapes of the tubes (2,3), making these blunt and pleasant to the touch for oral mucosa and the tongue.

Each tube (2, 3) has both its ends open. In each cleaning channel (14) one can appreciate two cleaning ailerons, each of which is provided with flexible and elastic dragging items (10) such as bristles, protrusions and scraping rasps, which press against the tooth due to the elastic nature of the device.

The device according to the invention can vary as regards its shape, size and length, and can be either short and straight in the preferential embodiment, for cleaning a few teeth at the same time (FIGS. 1a and 2d) or be in a curved shape with longer length, in what is known as the arched anatomical model or "U" shaped item (FIGS. 7a and 7b) for cleaning the entire dental arch in a single process.

The surface of the device may have a continuous surface along the tube or be discontinuous, forming annular fragments, for example.

To conclude, this invention is suitable for solving the problems described at the beginning of this description, as it focuses on taking advantage of simple chewing or biting movements, as well as the jaws' own force, for self-cleaning of the teeth, descaling and removing any food remains adhering to the surface of the teeth or bacterial plaque and around this (gums, lips, tongue and inter-dental space) on condition that these can be mechanically removed. This is compatible with the use of a paste or gel, mouthwashes or other dental cleaning substances or merely with one's own saliva.

What is claimed is:

1. A chewing-based oral self-cleaning device, comprising:
a semi-rigid elongated body comprising two tubes forming a frame with one of a cylindrical and prismatic section,
a base plate,
buffer strips at the base plate,
the tubes including a set of cleaning, massage and dragging items selected from the group of:
bristles,
protrusions, and
scraping rasps,
each tube having a semi-rigid, flexible and elastic body, formed as a slotted tube grooved in a longitudinal direction thereof to form a slot, each forming a cleaning channel tangentially superimposed relative to the longitudinal direction,
the two tubes and the base plate collectively forming a shape of a curved capital "H",
the two tubes being joined together one of
directly and
by the base plate,
two edges of each tube forming the respective slot extending towards an interior of the channel to form two cleaning ailerons adapted to elastically deform when a tooth arch pushes and penetrates between these two cleaning ailerons until the tooth arch reaches the buffer strips at the base plate, and
the cleaning ailerons and the base plate are provided with said cleaning, massage and dragging items, securely fitted and located so that said cleaning, massage and dragging items act elastically when they reach a surface area of teeth and gums when the teeth and gums move during mastication.

2. A chewing-based oral self-cleaning device, according to claim 1, wherein the tubes are fitted with an elastomeric casing.

3. A chewing-based oral self-cleaning device, according to claim 1, wherein an outer side of the base plate comprises an external fitting handle.

4. A chewing-based oral self-cleaning device, according to claim 1, further comprising a positioning flange one of:
between the tubes and
at a rear of the base plate.

5. A chewing-based oral self-cleaning device, according to claim 1, wherein the tubes are open at opposite ends thereof, forming a drain for remains from cleaning out an oral cavity.

6. A chewing-based oral self-cleaning device, according to claim 1, wherein the tubes comprise items on outer surfaces thereof for scraping and massaging gums and other soft parts of a mouth.

7. A chewing-based oral self-cleaning device, according to claim 1, wherein each tube includes a tubular wall which forms a continuous surface.

8. A chewing-based oral self-cleaning device, according to claim 1, wherein each tube includes a tubular wall which forms a discontinuous surface.

9. A chewing-based oral self-cleaning device, according to claim 1, further comprising a mechanism for adjustment of elastic tension of the tubes.

10. A chewing-based oral self-cleaning device, according to claim 9, wherein the mechanism for adjustment of the elastic tension of the tubes includes a screw-type regulator applied by a handle which exerts rotatory ram-like pressure on walls of the tubes.

11. A chewing-based oral self-cleaning device, according to claim 9, wherein the mechanism for adjustment of the elastic tension of the tubes is fitted longitudinally in respect of an axis of the tubes from a regulator in the base plate, and provides tightening which makes walls, edges and cleaning ailerons of the tubes converge with each other.

12. A chewing-based oral self-cleaning device, according to claim 1, wherein the device is rectilinear and is adapted to allow several teeth inside.

13. A chewing-based oral self-cleaning device, according to claim 1, wherein the device is curvilinear and is adapted to allow an entire tooth arch inside.

* * * * *